United States Patent
Lewis

(10) Patent No.: US 8,466,128 B2
(45) Date of Patent: Jun. 18, 2013

(54) HYALURONATE COMPOSITIONS

(75) Inventor: Robert Lewis, Madison, MS (US)

(73) Assignee: Cypress Pharmaceuticals, Inc., Madison, MS (US)

( * ) Notice: Subject to any disclaimer, the term of this patent is extended or adjusted under 35 U.S.C. 154(b) by 1369 days.

(21) Appl. No.: 12/022,095

(22) Filed: Jan. 29, 2008

(65) Prior Publication Data

US 2008/0119437 A1 May 22, 2008

Related U.S. Application Data

(60) Provisional application No. 60/898,297, filed on Jan. 30, 2007.

(51) Int. Cl.
*A61K 31/70* (2006.01)
*A61K 31/715* (2006.01)
*A61K 47/00* (2006.01)

(52) U.S. Cl.
USPC ............... 514/62; 514/53; 514/859; 514/861; 514/863; 514/865; 514/886

(58) Field of Classification Search
USPC ............. 514/62, 53, 859, 861, 863, 865, 886
See application file for complete search history.

(56) References Cited

U.S. PATENT DOCUMENTS

| | | |
|---|---|---|
| 3,396,081 A | 8/1968 | Billek |
| 4,141,973 A | 2/1979 | Balazs |
| 4,517,295 A | 5/1985 | Bracke et al. |
| 4,736,024 A | 4/1988 | Della Valle et al. |
| 4,784,900 A | 11/1988 | Carl et al. |
| 4,808,576 A | 2/1989 | Schultz et al. |
| 5,340,579 A | 8/1994 | Casero |
| 5,432,167 A * | 7/1995 | Brismar ............................ 514/54 |
| 5,563,051 A | 10/1996 | Ellwood et al. |
| 5,670,547 A * | 9/1997 | Milstein et al. ................ 514/725 |
| 5,985,850 A * | 11/1999 | Falk et al. ......................... 514/54 |
| 6,387,383 B1 * | 5/2002 | Dow et al. ...................... 424/401 |
| 7,314,634 B2 * | 1/2008 | Hernandez et al. ............ 424/401 |
| 2007/0172442 A1 * | 7/2007 | Saurat et al. ............... 424/70.13 |

FOREIGN PATENT DOCUMENTS

| | | |
|---|---|---|
| EP | 0244757 A2 | 11/1987 |
| EP | 1393749 A1 | 3/2004 |
| FR | 2865651 A1 | 8/2005 |
| JP | 2000230001 A * | 8/2000 |
| WO | WO-03071264 A1 | 8/2003 |
| WO | WO-2008/015249 A2 | 2/2008 |
| WO | WO-2008/072905 A1 | 6/2008 |
| WO | WO-2008/094910 A2 | 8/2008 |

OTHER PUBLICATIONS

Brimacombe, J., et al, "Molecular Weight and Shape," Mucopolysaccharides, Elsevier, XP002498228, p. 47-48, 1964.
International Search Report for International Application No. PCT/US08/52316, mailed Oct. 14, 2008.
Peixue Ling et al, Chemical Abstracts Service, Columbus, Ohio, US; XP002498230; Database accession No. 133: 256552 abstract, 2000.
Written Opinion of the International Searching Authority for International Patent Application No. PCT/US08/52316, mailed Oct. 14, 2008.
Yun Gi Cho et al., Chemical Abstracts Service, Columbus, Ohio, US; XP002498229; Database accession No. 137: 315740 abstract, 2001.

* cited by examiner

*Primary Examiner* — Wu-Cheng Winston Shen
*Assistant Examiner* — Everett White
(74) *Attorney, Agent, or Firm* — Fangli Chen; Justin P. Huddleson; Choate Hall & Stewsart, LLP

(57) ABSTRACT

The present invention provides compositions suitable for topical administration to a mammalian subject including sodium hyaluronate and a pharmaceutically acceptable excipient. The present invention also provides methods for malting and using the same.

56 Claims, No Drawings

HYALURONATE COMPOSITIONS

REFERENCE TO RELATED APPLICATIONS

This application claims the benefit of U.S. Provisional Patent Application No. 60/898,297, filed on Jan. 30, 2007, the contents of which are hereby incorporated by reference in their entireties.

FIELD OF THE INVENTION

The invention relates to compositions and methods for treating skin disorders, and for maintaining or enhancing the moisture of skin. In particular, the invention relates to compositions that contain hyaluronic acid and/or its salt as an active ingredient, and methods of using and making the same.

BACKGROUND OF THE INVENTION

Typically, for the treatment of skin diseases such as xerosis senilis and miliaria, adrenocortical steroid-based agents, urea-based ointments, heparinoids from animal organs, or vaselin-based ointments such as azulene ointments, have been used. However, most of these agents have undesirable side effects. For example, the adrenocortical steroid-based agents are likely to cause various side effects. The urea-based ointments sometimes cause irritation or smarting. The heparinoids from animal organs sometimes cause a contact dermatitis as a side effect. On the other hand, the vaselin-based ointments such as azulene ointments present unpleasant sticky feeling. In addition, dusts are likely to deposit on vaselin-based ointments. Thus, there have been no satisfying treatment agents for skin diseases.

SUMMARY OF THE INVENTION

The present invention provides improved compositions and methods for treating skin disorders or for maintaining or enhancing the moisture of skin. The compositions and methods of the present invention have better therapeutic effects and are safer and pleasant to use.

Thus, in one aspect, the present invention provides a composition suitable for topical administration to a mammalian subject (e.g., human) that contains sodium hyaluronate. In some embodiments, the composition includes, by mass, from about 0.05% to about 5% sodium hyaluronate and a pharmaceutically acceptable excipient. In certain embodiments, the pharmaceutically acceptable excipient is predominantly in the liquid phase at ambient temperature. In certain embodiments, from about 0.001 wt % to about 5 wt % of the sodium hyaluronate in the composition has a molecular weight ranging between about 0.01 megadaltons and about 0.4 megadaltons. In certain embodiments, from about 0.001 wt % to about 5 wt % of the sodium hyaluronate in the composition has a molecular weight ranging between about 0.5 megadaltons and about 1.6 megadaltons. In certain embodiments, from about 50 wt % to about 95 wt % of the sodium hyaluronate in the composition has a molecular weight ranging between about 1.7 megadaltons and about 4.0 megadaltons. As used in this application, "wt %", or "%" represents weight/weight percentage. "wt %" and "%" are used interchangeably herein.

In one embodiment, the present invention provides a composition suitable for topical administration to a mammalian subject (e.g., human) including, by mass, from about 0.05% to about 5% sodium hyaluronate and a pharmaceutically acceptable excipient, wherein from about 0.001 wt % to about 5 wt % of the sodium hyaluronate in the composition has a molecular weight ranging between about 0.01 megadaltons and about 0.4 megadaltons, from about 0.001 wt % to about 5 wt % of the sodium hyaluronate in the composition has a molecular weight ranging between about 0.5 megadaltons and about 1.6 megadaltons, from about 50 wt % to about 95 wt % of the sodium hyaluronate in the composition has a molecular weight ranging between about 1.7 megadaltons and about 4.0 megadaltons, and wherein the pharmaceutically acceptable excipient is predominantly in the liquid phase at ambient temperature. As used herein, "1 megadalton" equals 1 million Daltons (i.e., 1,000,000 daltons).

In some embodiments, the pharmaceutically acceptable excipient suitable for the present invention is selected from the group consisting of water, an alcohol, an oil, glycerin, polyethylene glycol, lanolin, petrolatum, wax, and poloxamer.

In certain embodiments, the pharmaceutically acceptable excipient is an alcohol. In certain embodiments, the pharmaceutically acceptable excipient is an alcohol selected from the group consisting of ethanol, benzyl alcohol, isopropyl alcohol, octyldodecanol, cetostearyl alcohol, and lanolin alcohol.

In certain embodiments, the pharmaceutically acceptable excipient is an oil. In certain embodiments, the pharmaceutically acceptable excipient is an oil selected from the group consisting of almond oil, castor oil, corn oil, cottonseed oil, light mineral oil, mineral oil, olive oil, peanut oil, polyoxyl 35 castor oil, sesame oil, soybean oil, and sunflower oil. In some embodiments, the pharmaceutically acceptable excipient includes white petrolatum.

In certain embodiments, the pharmaceutically acceptable excipient is water. In certain embodiments, the ratio of the mass of water to the total mass of the composition is about 50% or greater, about 55% or greater, about 60% or greater, about 65% or greater, about 70% or greater, about 75% or greater, about 80% or greater, about 85% or greater, about 90% or greater, about 95% or greater, about 96% or greater, about 97% or greater, about 98% or greater, about 99% or greater, about 99.5% or greater. In certain embodiments, the ratio of the mass of water to the total mass of the composition ranges from about 60% to about 99.9%. In certain embodiments, the ratio of the mass of water to the total mass of the composition ranges from about 90.0% to about 99.9%. In certain embodiments, the ratio of the mass of water to the total mass of the composition ranges from about 92.5% to about 99.8%. In certain embodiments, the ratio of the mass of water to the total mass of the composition ranges from about 95.0% to about 99.7%. In certain embodiments, the ratio of the mass of water to the total mass of the composition ranges from about 97.5% to about 99.6%. In certain embodiments, the ratio of the mass of water to the total mass of the composition ranges from about 98.5% to about 99.5%. In certain embodiments, the ratio of the mass of water to the total mass of the composition ranges from about 99.0% to about 99.4%. In certain embodiments, the ratio of the mass of water to the total mass of the composition ranges from about 99.2% to about 99.3%. In certain embodiments, the ratio of the mass of water to the total mass of the composition is about 99.235%.

In some embodiments, the composition further includes an antifungal agent. In certain embodiments, the antifungal agent suitable for the invention is selected from the group consisting of clioquinol, haloprogin, miconazole nitrate, povidone-iodine, tolnaftate, ketoconazole, undecylenic acid, butoconazole and clotrimazole. In one embodiment, the antifungal agent suitable for the invention is clotrimazole.

In some embodiments, the composition further includes an antibiotic. In certain embodiments, the antibiotic suitable for the invention is selected from the group consisting of bacitracin, bacitracin zinc, chlortetracycline hydrochloride, neomycin sulfate, clindamycin, erythromycin, and tetracycline hydrochloride.

In some embodiments, the composition further includes an anti-acne agent. In certain embodiments, the anti-acne agent suitable for the invention is selected from the group consisting of benzoyl peroxide, resorcinol, resorcinol monoacetate, salicylic acid, sulfur, adapalene, alitretinoin, etretinate, isotretinoin, tazarotene, and tretinoin. In certain embodiments, the anti-acne agent is benzoyl peroxide. In certain embodiments, the ratio of the mass of benzoyl peroxide to the total mass of the composition ranges from about 2.5% to about 10%.

In some embodiments, the composition further includes an antiviral agent. In some embodiments, the composition further includes butylated hydroxytoluene. In some embodiments, the composition further includes butylated hydroxyanisole. In some embodiments, the composition includes white petrolatum and butylated hydroxytoluene. In certain embodiments, the composition includes white petrolatum and butylated hydroxyanisole.

In certain embodiments, the composition further includes one or more ceramides. In certain embodiments, the composition further includes a corticosteroid. In certain embodiments, the corticosteroid is selected from the group consisting of betamethasone valerate, betamethasone dipropionate, dexamethasone acetate, dexamethasone sodium phosphate, hydrocortisone, hydrocortisone acetate, and hydrocortisone butyrate.

In some embodiments, the composition has an apparent viscosity of from about 5,000 to about 300,000 centipoise. In some embodiments, the composition has an apparent viscosity of from about 10,000 to about 300,000 centipoise. In some embodiments, the composition has an apparent viscosity of from about 10,000 to about 20,000 centipoise.

In some embodiments, the pH of the composition ranges from about 4 to about 8.

In another aspect, the present invention provides a composition suitable for maintaining or enhancing the moisture of skin. In some embodiments, the composition includes, by mass, at least about 80% water; sodium hyaluronate; one or more preservatives; one or more thickening agents; and one or more bases; wherein the ratio of the mass of sodium hyaluronate to the total mass of the composition is about 0.05%, 0.1%, 0.15%, 0.2%, 0.25%, 0.3%, 0.35%, 0.4%, 0.45%, or 0.5%. In one embodiment, the ratio of the mass of sodium hyaluronate to the total mass of the composition is about 0.1%.

In some embodiments, the sodium hyaluronate has a molecular weight between about 1.6 million Daltons (i.e., 1.6 megadaltons) and about 2.8 million Daltons (i.e., 2.8 megadaltons).

In some embodiments, the one or more preservatives suitable for the invention are selected from the group consisting of methylparaben, propylparaben, edetate sodium, benzalkonium chloride, and benzyl alcohol. In certain embodiments, the one or more preservatives include methylparaben. In certain embodiments, the one or more preservatives include propylparaben. In certain embodiments, the one or more preservatives include methylparaben and propylparaben.

In some embodiments, the one or more thickening agents suitable for the invention are selected from the group consisting of carbomer 940, methyl cellulose, xanthan gum, carboxymethyl cellulose, hydroxypropyl cellulose, polyvinyl alcohol, one or more alginates, acacia, and one or more chitosans. In certain embodiments, the one or more thickening agents include carbomer 940.

In some embodiments, the one or more bases suitable for the invention are selected from the group consisting of trolamine, sodium hydroxide, sodium bicarbonate, potassium hydroxide, magnesium hydroxide, calcium hydroxide, ammonium hydroxide, and potassium bicarbonate. In certain embodiments, the one or more bases include trolamine.

In some embodiments, the pH of the composition is between about 4 and about 8.

In some embodiments, the composition has an absorbance of not more than 0.1 at 600 nm and a path of 1.0 cm. In some embodiments, the composition has a viscosity measured at temperature of 25 degree Celsius of not less than 5,000 centipoise and not more than 100,000 centipoise. In some embodiments, the composition has an absorbance of not more than 0.1 at 600 nm and a path of 1.0 cm and a viscosity measured at temperature of 25 degree Celsius of not less than 5,000 centipoise and not more than 100,000 centipoise.

In yet another aspect, the present invention provides a composition suitable for maintaining or enhancing the moisture of skin, including, by mass, at least about 90% water; sodium hyaluronate; methylparaben; propylparaben; carbomer 940; and trolamine, wherein the ratio of the mass of sodium hyaluronate to the total mass of the composition is about 0.05% to 0.3%.

In some embodiments, the sodium hyaluronate has a molecular weight between about 1.6 million Daltons (i.e., 1.6 megadaltons) and about 2.8 million Daltons (i.e., 2.8 megadaltons).

In still another aspect, the present invention provides a composition suitable for maintaining or enhancing the moisture of skin, including, by mass, at least about 95% water; 0.1% sodium hyaluronate; one or more preservatives; one or more thickening agents; and one or more bases; wherein the composition has an absorbance of not more than 0.1 at 600 nm and a path of 1.0 cm and wherein the composition has a viscosity measured at temperature of 25 degree Celsius of not less than 5,000 centipoise and not more than 300,000 centipoise. In some embodiments, the composition of the invention has a viscosity measured at temperature of 25 degree Celsius of not less than 10,000 centipoise and not more than 200,000 centipoise. In some embodiments, the composition of the invention has a viscosity measured at temperature of 25 degree Celsius of not less than 10,000 centipoise and not more than 20,000 centipoise. In some embodiments, the composition of the invention has a viscosity measured at temperature of 25 degree Celsius of not less than 11,000 centipoise and not more than 18,000 centipoise. In some embodiments, the sodium hyaluronate has a molecular weight between about 1.6 million Daltons and about 2.8 million Daltons.

In a further aspect, the present invention provides a composition suitable for maintaining or enhancing the moisture of skin, consisting essentially of, by mass, at least about 99% water; about 0.1% sodium hyaluronate; one or more preservatives; one or more thickening agents; and one or more bases.

In some embodiments, the sodium hyaluronate has a molecular weight between about 1.6 million Daltons and about 2.8 million Daltons.

In still another aspect, the present invention provides a composition suitable for maintaining or enhancing the moisture of skin, consisting essentially of, by mass, about 0.1% sodium hyaluronate, about 0.2% methylparaben, about 0.02% propylparaben, about 0.3% carbomer 940, about 0.15% trolamine, and about 99.23% water.

In some embodiments, the sodium hyaluronate has a molecular weight between about 1.6 million Daltons and about 2.8 million Daltons.

Combinations of various embodiments described above are within the scope the invention. The present invention further encompasses the use of the composition as described in various embodiments above in skin disorder therapy. The present invention also encompasses the use of the composition of as described in various embodiments above for the manufacture of a medicament for the treatment of skin disorder.

Thus, in one aspect, the present invention provides a method for treating a skin disorder on a mammalian subject (e.g., human). In some embodiments, the method includes administering to a subject an effective amount of the composition of the present invention, in particular, as described in various embodiments above.

In some embodiments, the present invention can be used to treat a skin disorder selected from the group consisting of eczema, dermatitis, atopic dermatitis, xerosis, psoriasis, inflammation, diaper rash, fungal infection and acne.

In some embodiments, the composition is administered at least once per day. In some embodiments, the composition is administered at least twice per day. In some embodiments, the composition is administered three times per day.

In another aspect, the present invention provides a process for manufacturing a composition of the invention. In some embodiments, the process includes the steps of: (a) admixing one or more preservatives, sodium hyaluronate, and one or more thickening agents to form a pre-water mixture; (b) admixing one or more bases and water to form a water mixture; (c) admixing the pre-water mixture and the water mixture to form a post-water mixture; and (d) homogenizing the post-water mixture to form the composition.

In some embodiments, step (a) includes admixing methylparaben, propylparaben, sodium hyaluronate, and carbomer 940 in an approximate ratio, by mass, of 0.2:0.02:0.1:0.3 to form the pre-water mixture.

In some embodiments, step (b) includes admixing trolamine and water in an approximate ratio, by mass, of 0.15:99.23 to form the water mixture.

In some embodiments, step (c) includes admixing the pre-water mixture and the water mixture in an approximate ratio, by mass, of 0.62:99.38, to form a post-water mixture.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

DETAILED DESCRIPTION OF THE INVENTION

The present invention provides improved compositions and methods for treating skin disorders or for maintaining or enhancing the moisture of skin. A composition according to the invention includes hyaluronic acid or its salt (e.g., sodium hyaluronate) as an active ingredient and one or more pharmaceutically acceptable excipients. In particular, a composition according to the invention may contain a very high proportion of water by mass. As a result, the composition of the invention is not only therapeutically effective in treating skin disorders, but also has certain consumer-appealing characteristics, such as clarity and suitable viscosity, over the course of time, and lacks certain unappealing characteristics, such as greasiness.

Various aspects of the invention are described in detail in the following sections. The use of sections is not meant to limit the invention. Each section can apply to any aspect of the invention. In this application, the use of "or" means "and/or" unless stated otherwise.

Hyaluronic Acid and its Salt

The source of the hyaluronate used in the present invention may be a hyaluronic acid or any acceptable salt form of hyaluronic acid. As used herein, the term "hyaluronate" means hyaluronic acid and its equivalents, which includes hyaluronic acid of varying molecular weights and any of their salt forms, such as sodium hyaluronate.

Hyaluronic acid is a linear mucopolysaccharide comprised of alternating glucuronic acid and N-acetyl-glucosamine residues that interact with other proteoglycans to provide stability and elasticity to the extracellular matrix of all tissues. This network of macromolecules regulates tissue hydration and the movement of substances within the interstitial compartment.

Hyaluronic acid may be used in the form of an acid, or in the form of a hyaluronic acid salt. Suitable salt form includes, but is not limited to, an alkali metal salt such as a sodium or potassium salt, an alkaline earth metal salt such as a magnesium or calcium salt. In particular, a sodium salt, i.e., sodium hyaluronate is used in the present invention.

Hyaluronic acid can be obtained from an extract of, for example, a cockscomb, a viterous body or an umbilical code, or from a culture of certain bacteria such as a hyaluronic acid-producing microorganism of Genus *streptococcus*. Hyaluronic acid can be used for the present invention irrespective of its origin. In some embodiments, hyaluronic acid used for the present invention can be obtained from the culture of a hyaluronic acid-producing microorganism. High molecular weight and high purity hyaluronic acid and its salt forms can be obtained using this method.

Methods of obtaining highly-pure or ultra-pure hyaluronic acid and its salt forms, isolation techniques, and analytical methods for testing purity are provided, for example, in the U.S. Pat. Nos. 3,396,081, 4,141,973, 4,517,295, 4,736,024, 4,784,900 and 4,808,576, the teachings of which are hereby incorporated by reference.

It is contemplated that sodium hyaluronate from any of a number of sources may be used as a starting material in making a composition according to the invention. For example, Proturon™ Standard-C sodium hyaluronate-2222200 from FMC Biopolymer (1735 Market Street, Philadelphia, Pa. 19103) may be used as a starting material.

A composition of the invention may contain sodium hyaluronate at various concentrations. Typically, a suitable concentration of sodium hyaluronate in the composition ranges from, by mass, about 0.001 wt % to 5.0 wt %. In certain embodiments, a suitable concentration of sodium hyaluronate in the composition ranges from, by mass, about 0.05 wt % to 5.0 wt %. In certain embodiments, a suitable concentration of sodium hyaluronate in the composition ranges from, by mass, about 0.05 wt % to 0.3 wt %. In certain embodiments, a suitable concentration of sodium hyaluronate in the composition ranges from, by mass, about 0.05 wt % to 1.5 wt %. In certain embodiments, a suitable concentration of sodium hyaluronate in the composition is about 0.1 wt %.

Typically, sodium hyaluronate suitable for the invention may have a molecular weight ranging between about 10,000 daltons and 8,000,000 daltons, or higher. In particular, suitable sodium hyaluronate has a molecular weight ranging between about 10,000 daltons and 400,000 daltons; between about 500,000 daltons and 1,600,000 daltons; between about 1,700,000 daltons and 4,000,000 daltons; between about 1,600,000 daltons and 2,800,000 daltons; between about 800,000 daltons and 4,000,000 daltons; or between about 1,000,000 daltons and 3,000,000 daltons.

Without wishing to be bound by any theory, it is contemplated that the physicochemical and/or physiological properties of sodium hyaluronate vary according to the molecular weight of the molecule. For example, the physicochemical properties of sodium hyaluronate having a molecular weight of, for example, ten thousand Daltons, differ appreciably from the physicochemical properties of sodium hyaluronate having a molecular weight of four million Daltons. Also, the physiological properties of sodium hyaluronate having a molecular weight of, for example, ten thousand Daltons, differ appreciably from the physiological properties of sodium hyaluronate having a molecular weight of four million Daltons. Without wishing to be bound by any theory, it is also contemplated that sodium hyaluronate having a small molecular weight provides less moisturizing effect, and sodium hyaluronate having a molecular weight of 4,000,000 daltons or larger tends to be highly viscous, whereby formulation will be difficult.

Thus, it is desirable to provide a composition that includes a blend of sodium hyaluronate of various molecular weights, given the large variation in physicochemical and physiological properties of sodium hyaluronate of differing molecular weights. For example, a composition according to the invention may include a blend of sodium hyaluronate with one or more combinations of the following: from about 0.001 wt % to about 5 wt % of the sodium hyaluronate in the composition has a molecular weight of between about 0.01 and about 0.4 megadaltons; and/or from about 0.001 wt % to about 5 wt % of the sodium hyaluronate in the composition has a molecular weight of between about 0.5 megadaltons and about 1.6 megadaltons; and/or from about 50 wt % to about 95 wt % of the sodium hyaluronate in the composition has a molecular weight of between about 1.7 megadaltons and about 4.0 megadaltons. As used herein, "wt %" or "%" is weight/weight percentage.

Formulations

A composition of the present invention may be formulated into various forms. For example, the composition of the invention may be formulated into a lotion, an aqueous solution, an emulsifiable ointment, or a water-soluble ointment. It may be formulated in accordance with various formulation methods known in the art.

Typically, a composition of the invention is clear and suitably viscous, As used in connection with the invention, "clear" refers to the quality of having an absorbance of not more than 0.1 at 600 nm n, where absorbance is measured at a temperature of 22.5±3.5 degrees Celsius (in other words, at any temperature not less than 19.0 degrees Celsius and not more than 26.0 degrees Celsius), and where the path length is 1.0 cm. As used herein, the term "absorbance" refers to a measure of the proportion of light absorbed and/or scattered by a fluid, and typically measured in a spectrophotometer. Typically, absorbance refers to the base ten logarithm of the ratio of the light intensity transmitted by a liquid water reference sample (or "blank") to the light intensity transmitted by the sample under analysis, which in this case is a sample of a composition according to the invention. Purified water USP is used as a blank in this instance.

As used in connection with the invention, "suitably viscous" refers to the quality of having a viscosity, measured at a temperature of 25 degrees Celsius, of not less than 5,000 centipoise and not more than 300,000 centipoise. For example, a suitable viscosity includes a viscosity, measured at a temperature of 25 degrees Celsius, ranging from about 5,000 to about 300,000 centipoise, from about 5,000 to about 200,000 centipoise, from about 5,000 to about 100,000 centipoise, from about 10,000 to about 200,000 centipoise, from about 10,000 to about 100,000 centipoise, from about 10,000 to about 20,000 centipoise, or from about 11,000 to about 18,000 centipoise. As used herein, the term "viscosity" refers to a measure of the internal friction of a fluid, and typically measured in a viscometer. Typically, viscosity is the ratio of shear stress (measured in dynes per square centimeter) to shear rate (measured in reciprocal seconds). A poise, which is equal to 100 centipoise, equals one dyne-second per square centimeter.

As used in connection with the invention, "lotion" refers to a composition useful for application to one or more areas of skin of a human subject in order to maintain and/or enhance the moisture of the one or more areas of skin. As used herein, the term "application" refers to contacting the composition with the one or more areas of skin and may include spreading the composition across the one or more areas of skin and/or rubbing the composition into the one or more areas of skin.

Analytical methods used in connection with the invention are those known in the pharmaceutical arts.

Typically, in addition to active ingredient, hyaluronic acid or its salt form, a suitable formulation of the invention may include one or more pharmaceutically acceptable exicipients, preservatives, thickening agents, bases, moisturizing agents, antifungal agents, antibiotics, anti-acne agents, stabilizing agents, or other components commonly used for treating skin diseases or maintaining or enhancing the moisture of skin.

Typically, a composition of the invention includes a pharmaceutically acceptable excipient. In particular, a pharmaceutically acceptable excipient suitable for the invention is predominantly in the liquid phase at ambient temperature. Exemplary excipients suitable for the invention include, but are not limited to, water, alcohol, oil, glycerin, polyethylene glycol, lanolin, petrolatum, wax, and poloxamer.

In certain embodiments, a pharmaceutically acceptable excipient is an alcohol. Suitable alcohols include, but are not limited to, ethanol, benzyl alcohol, isopropyl alcohol, octyldodecanol, cetostearyl alcohol, and lanolin alcohol.

In certain embodiments, a pharmaceutically acceptable excipient is oil. Suitable oils include, but are not limited to, almond oil, castor oil, corn oil, cottonseed oil, light mineral oil, mineral oil, olive oil, peanut oil, polyoxyl 35 castor oil, sesame oil, soybean oil, and sunflower oil.

In some embodiments, a pharmaceutically acceptable excipient may include white petrolatum.

In some embodiments, a pharmaceutically acceptable excipient is water. Typically, a composition of the invention contains a high percentage of water. For example, the ratio of the mass of water to the total mass of the composition may be about 50% or greater, about 55% or greater, about 60% or greater, about 65% or greater, about 70% or greater, about 75% or greater, about 80% or greater, about 85% or greater, about 90% or greater, about 95% or greater, about 96% or greater, about 97% or greater, about 98% or greater, about 99% or greater, about 99.5% or greater. In certain embodiments, the ratio of the mass of water to the total mass of the composition may range from about 60% to about 99.9%. In certain embodiments, the ratio of the mass of water to the total mass of the composition ranges from about 90.0% to about 99.9%. In certain embodiments, the ratio of the mass of water to the total mass of the composition ranges from about 92.5% to about 99.8%. In certain embodiments, the ratio of the mass of water to the total mass of the composition ranges from about 95.0% to about 99.7%. In certain embodiments, the ratio of the mass of water to the total mass of the composition ranges from about 97.5% to about 99.6%. In certain embodiments, the ratio of the mass of water to the total mass of the composition ranges from about 98.5% to about 99.5%. In certain embodiments, the ratio of the mass of water to the total mass of the composition ranges from about 99.0% to about 99.4%. In certain embodiments, the ratio of the mass of water to the total mass of the composition ranges from about 99.2% to about 99.3%. In certain embodiments, the ratio of the mass of water to the total mass of the composition is about 99.235%.

Typically, a composition of the invention may contain one or more preservatives. Suitable preservatives for the invention include, but are not limited to, methylparaben, propylparaben, edetate sodium, benzalkonium chloride, and benzyl alcohol. Generally, any preservatives known in the art can be used for the invention.

A composition of the invention may contain one or more thickening agents. Suitable thickening agents for the invention include, but are not limited to, carbomer 940, methyl cellulose, xanthan gum, carboxymethyl cellulose, hydroxypropyl cellulose, polyvinyl alcohol, one or more alginates, acacia, and/or one or more chitosans. Generally, any thickening agents known in the art can be used for the invention.

A composition of the invention may contain one or more bases. Suitable bases include, but are not limited to, trolamine, sodium hydroxide, sodium bicarbonate, potassium hydroxide, magnesium hydroxide, calcium hydroxide, ammonium hydroxide, and potassium bicarbonate. Generally, any bases known in the art can be used for the invention.

A composition of the invention may include an antifungal agent. Suitable antifungal agents include, but are not limited to, clioquinol, haloprogin, miconazole nitrate, povidone-iodine, tolnaftate, ketoconazole, undecylenic acid, butoconazole and clotrimazole. In one embodiment, the antifungal agent suitable for the invention is clotrimazole.

A composition of the invention may include an antibiotic. Suitable antibiotics include, but are not limited to, bacitracin, bacitracin zinc, chlortetracycline hydrochloride, neomycin sulfate, clindamycin, erythromycin, and tetracycline hydrochloride.

A composition of the invention may include an anti-acne agent. Suitable anti-acne agents include, but are not limited to, benzoyl peroxide, resorcinol, resorcinol monoacetate, salicylic acid, sulfur, adapalene, alitretinoin, etretinate, isotretinoin, tazarotene, and tretinoin. In certain embodiments, the anti-acne agent is benzoyl peroxide. Anti-acne agents, such as benzoyl peroxide, can be included at various concentrations. For example, the ratio of the mass of benzoyl peroxide to the total mass of the composition may range from about 2.5% to about 10%.

A composition of the invention may include an antiviral agent. Suitable antiviral agents include, but are not limited to, butylated hydroxytoluene, butylated hydroxyanisole, butylated hydroxytoluene.

A composition of the invention may include one or more ceramides. Suitable ceramides include, but are not limited to, Types I to VII, N-oleoyl-sphingosine, N-(12-hydroxyoctadecanoyl)sphingosine, N-(16-hydroxyhexadecanoyl)sphingosine and bovine brain ceramide.

A composition of the invention may include a corticosteroid. Suitable corticosteroids include, but are not limited to, betamethasone valerate, betamethasone dipropionate, dexamethasone acetate, dexamethasone sodium phosphate, hydrocortisone, hydrocortisone acetate, and hydrocortisone butyrate.

Typically, the pH of a composition ranges between about 4 and about 8. For example, the pH of a composition according to the invention can be about 4.0, about 4.5, about 5.0, about 5.5, about 6.0, about 6.5, about 7.0, about 7.2, about 7.5, or about 8.0.

As an example, the invention provides a clear, suitably viscous lotion composition consisting essentially of, by mass, at least about 99% water; about 0.1% sodium hyaluronate; one or more preservatives; one or more thickening agents, and one or more bases. For example, the pH of the composition may be between about 4 and about 8.

As another example, a composition according to the invention may consist essentially of one or more preservatives, about 0.1%, by mass, sodium hyaluronate having molecular weight substantially between about 1.6 million and about 2.8 million Daltons, one or more thickening agents, one or more bases, and at least about 99%, by mass, water. Such a composition is useful as a lotion and is clear and suitably viscous.

As a further example, a composition according to the invention consisted essentially of, by mass, about 0.2% methylparaben NF, about 0.02% propylparaben NF, about 0.1% sodium hyaluronate having molecular weight substantially between about 1.6 million and about 2.8 million Daltons, about 0.3% carbomer 940 NF, about 0.15% trolamine NF, and about 99.23% purified water USP. Such a composition was useful as a lotion and was clear and suitably viscous.

As yet another example, a composition according to the invention consists essentially of, by mass, from about 0.01% to about 0.1% edetate disodium USP, from about 0.01% to about 0.02% benzalkonium chloride NF, from about 0.1% to about 0.5% methylcellulose USP, from about 0.01% to about 0.3% sodium hydroxide NF, about 0.1% sodium hyaluronate having molecular weight substantially between about 1.6 million and about 2.8 million Daltons, and purified water USP q.s., wherein the composition has a pH of between about 4 and about 8. Such a composition is useful as a lotion and is clear and suitably viscous.

As another example, a composition according to the invention consists essentially of, by mass, from about 0.02% to about 0.5% sodium benzoate NF, from about 0.1% to about 0.2% potassium sorbate NF, from about 0.2% to about 0.5% xanthan gum NF, from about 0.01% to about 0.3% sodium phosphate monobasic, about 0.1% sodium hyaluronate having molecular weight substantially between about 1.6 million and about 2.8 million Daltons, and purified water USP q.s., wherein the composition has a pH of between about 4 and about 8. Such a composition is useful as a lotion and is clear and suitably viscous.

As another example, a composition according to the invention consists essentially of, by mass, from about 0.01% to about 0.02% benzalkonium chloride NF, from about 0.01% to about 0.3% benzyl alcohol NF, from about 0.2% to about 0.5% hydroxyethylcellulose NF, from about 0.01% to about 0.3% sodium hydroxide, about 0.1% sodium hyaluronate having molecular weight substantially between about 1.6 million and about 2.8 million Daltons, and purified water USP q.s., wherein the composition has a pH of between about 4 and about 8. Such a composition is useful as a lotion and is clear and suitably viscous.

Manufacturing Processes

Generally, a process for manufacturing a composition according to the invention includes admixing one or more preservatives, sodium hyaluronate, and one or more thickening agents to form a pre-water mixture; admixing one or more bases and water to form a water mixture; and admixing the pre-water mixture and the water mixture to form a post-water mixture. In general, the post-water mixture is homogenized until the post-water mixture is clear and suitably viscous. Accordingly, samples of the post-water mixture may be collected, for example, during its homogenization, and analyzed to determine whether the post-water mixture is clear and suitably viscous. A post-water mixture that is clear and suitably viscous is useful as a lotion.

As one example, a process for manufacturing a composition according to the invention includes admixing methylparaben, propylparaben, sodium hyaluronate, and carbomer 940 in the approximate ratio, by mass, of 0.2:0.02:0.1:0.3 to form a pre-water mixture; admixing trolamine and water in the approximate ratio, by mass, of 0.15:99.23 to form a water mixture; and admixing the pre-water mixture and the water mixture in the approximate ratio, by mass, of 0.62:99.38, to form a post-water mixture. In general the post-water mixture is homogenized until the post-water mixture is clear and suitably viscous. Accordingly, samples of the post-water mixture may be collected, for example during its homogenization, and analyzed to determine whether the post-water mixture is clear and suitably viscous. A post-water mixture that is clear and suitably viscous is useful as a lotion.

As another example, a process for manufacturing a composition according to the invention includes admixing edetate sodium, benzalkonium chloride, sodium hyaluronate, and methylcellulose in the approximate ratio, by mass, of 0.05:0.015:0.1:0.5 to form a pre-water mixture; admixing sodium hydroxide and water in the approximate ratio, by mass, of 0.3:98.9 to form a water mixture; and admixing the pre-water mixture and the water mixture in the approximate ratio, by mass, of 0.8:99.2, to form a post-water mixture. In general the post-water mixture is homogenized until the post-water mixture is clear and suitably viscous. Accordingly, samples of the post-water mixture may be collected, for example during its homogenization, and analyzed to determine whether the post-water mixture is clear and suitably viscous. A post-water mixture that is clear and suitably viscous is useful as a lotion.

As yet another example, a process for manufacturing a composition according to the invention includes admixing sodium benzoate, potassium sorbate, sodium hyaluronate, and xanthan gum in the approximate ratio, by mass, of 0.25:0.15:0.1:0.35 to form a pre-water mixture; admixing sodium phosphate monobasic and water in the approximate ratio, by mass, of 0.15:99 to form a water mixture; and admixing the pre-water mixture and the water mixture in the approximate ratio, by mass, of 0.85:99.15, to form a post-water mixture. In general the post-water mixture is homogenized until the post-water mixture is clear and suitably viscous. Accordingly, samples of the post-water mixture may be collected, for example during its homogenization, and analyzed to determine whether the post-water mixture is clear and suitably viscous. A post-water mixture that is clear and suitably viscous is useful as a lotion.

As a further example, a process for manufacturing a composition according to the invention includes admixing benzalkonium chloride, benzyl alcohol, sodium hyaluronate, and hydroxyethylcellulose in the approximate ratio, by mass, of 0.015:0.15:0.1:0.35 to form a pre-water mixture; admixing sodium hydroxide and water in the approximate ratio, by mass, of 0.15:99.235 to form a water mixture; and admixing the pre-water mixture and the water mixture in the approximate ratio, by mass, of 0.615:99.385, to form a post-water mixture. In general the post-water mixture is homogenized until the post-water mixture is clear and suitably viscous. Accordingly, samples of the post-water mixture may be collected, for example during its homogenization, and analyzed to determine whether the post-water mixture is clear and suitably viscous. A post-water mixture that is clear and suitably viscous is useful as a lotion.

A composition according to the invention can also be made according to various methods flown in the art. For example, components that are in the liquid phase at ambient temperature may be admixed to form a liquid admixture, and other components that are in the solid phase at ambient temperature may be admixed to form a solid admixture. The liquid admixture and the solid admixture can then admixed to form a liquid-solid admixture. Alternatively, it may be advantageous to first dissolve some sparingly soluble components, or some which, despite being very soluble, are slow to dissolve, in a suitable solvent. By way of example and not of limitation, for an aqueous formulation of sodium hyaluronate, it may be advantageous to admix sodium hyaluronate and water to form a sodium hyaluronate-water admixture, then add a liquid admixture and a solid admixture.

A composition according to the invention may be filled into an appropriate dispenser (e.g., a pumper dispenser) or other suitable containers by any automated filling equipment suitable for such purposes known in the art, or by hand, for storage or use.

Treatment of Skin Disorders

The composition of the invention can be used for maintaining or enhancing the moisture of skin. In particular, the composition of the invention can be used to treat a skin disorder on a mammalian subject, for example, a human patient.

Thus, the present invention provides a method for treating a skin disorder on a mammalian subject by administering to the subject an effective amount of a composition as described in various embodiments above. The composition of the invention may be used to treat a skin disorder including, but not limited to, eczema, dermatitis, atopic dermatitis, xerosis, psoriasis, inflammation, diaper rash, fungal infection and acne.

Typically, an effective amount is a liberal amount that, when administered at regular intervals, is sufficient to treat the skin disease, such as by ameliorating one or more symptoms associated with various skin diseases or disorders, for example, scaling, dryness, roughness, redness, sensitiveness, flaking of the skin. The amount which will be therapeutically effective for the treatment of the disease will depend on the nature and extent of the disease's effects, and can be decided according to the judgment of a practitioner and each patient's circumstances.

Typically, a composition according to the invention may be provided in an appropriate dispenser, such as a pump dispenser. A volume of the composition can be removed from the dispenser, placed into a hand, and administered topically to a skin area in need of treatment. For example, a volume containing an effective amount of a composition of the invention can be rubbed onto and/or into an area of a skin in need of treatment. The composition may be administered at least once a day, twice a day, three times a day, once every other day, twice a week, once a week, once every other week, or as needed.

The invention will be further and more specifically described by the following examples. Examples, however, are included for illustration purposes, not for limitation.

EXAMPLES

Example 1

Exemplary Compositions

Table 1 shows exemplary compositions containing a mixture of various molecular weights of sodium hyaluronate useful for the purposes of the invention.

The ratios of the molecular weights of sodium hyaluronate recited in Table 1 are considered optimal for the intended utility of a composition according to the invention.

TABLE 1

| Wt. % | <0.01 MDa | 0.01-0.45 MDa | 0.45-1.65 MDa | 1.65-4.0 MDa | >4.0 MDa |
|---|---|---|---|---|---|
| <0.001 | E | | | | E |
| 0.001 | | E | E | | |
| 0.01 | | E | E | | |
| 0.1 | | E | E | | |
| 1 | | E | E | | |
| 5 | | E | E | | |
| 50 | | | | | E |
| 95 | | | | | E |
| 99 | | | | | |
| 99.9 | | | | | |
| 99.99 | | | | | |
| 99.999 | | | | | |
| >99.999 | | | | | |

E denotes effective, or acceptable for the purposes of the invention

Example 2

Exempla Formulations

Table 2 shows exemplary formulations containing sodium hyaluronate and one or more other components (e.g., excipients). The exemplary formulations may be prepared according to the methods as described in the manufacturing processes above.

TABLE 2

Exemplary formulations
Weight/weight percentages are shown.

| Component | Miconazole A | NaHA B | Cerimide/ NaHa C | Clindamycin D | BPO E | Acyclovir F | Clotrimazole G | NaHA H | Cotico I | NaHa J |
|---|---|---|---|---|---|---|---|---|---|---|
| 0.5M MW Sodium Hyaloranate | 0.005 | 0.005 | 0.005 | 0.01 | 0.005 | 0.01 | 0.005 | 0.01 | 0.005 | 0.02 |
| 1.6M MW Sodium Hyaloranate | 0.01 | 0.01 | 0.01 | 0.02 | 0.01 | 0.02 | 0.01 | 0.02 | 0.01 | 0.04 |
| 2.2M MW Sodium Hyaloranate | 0.085 | 0.085 | 0.085 | 0.17 | 0.085 | 0.17 | 0.085 | 0.17 | 0.085 | 0.34 |
| Methylparaben | — | 0.2 | 0.2 | 0.2 | — | — | — | 0.2 | — | 0.2 |
| Benzoyl Peroxide | — | — | — | — | 5.0 | — | — | — | — | — |
| White Petrolatum | 82.0 | — | — | — | — | — | 82.0 | — | 81.48 | — |
| Polyethylene Glycol 400 | — | — | — | 5.5 | — | 40.8 | — | — | — | — |
| Propylparaben | — | 0.02 | 0.02 | — | — | — | — | 0.02 | — | 0.02 |
| Castor Oil | — | — | 0.9 | — | — | — | — | — | — | — |
| Zinc Oxide | 15.0 | — | — | — | — | — | 15.0 | — | — | — |
| Carbomer 940 | — | 0.6 | — | 0.3 | — | — | — | 0.4 | — | 0.3 |
| Betamethasone Valerate | — | — | — | — | — | — | — | — | 0.12 | — |
| Thixcin R | 3.0 | — | — | — | — | — | 3.0 | — | — | — |
| Cerimide 3 | — | — | 1.0 | — | — | — | — | — | — | — |
| Cetyl Alcohol | — | — | — | 1.0 | — | — | — | — | — | — |
| Clotrimazole | — | — | — | — | — | — | 0.75 | — | — | — |
| Carbomer 141 | — | — | 0.5 | — | — | — | — | — | — | — |
| Dimethicone | — | — | 0.9 | — | — | — | — | — | — | — |
| Glycerin | — | 0.02 | 3.0 | — | — | — | — | — | — | — |
| Mineral Oil | — | — | — | — | — | — | — | — | 18.3 | — |
| Glyeryl Sterarate | — | — | — | — | 3.0 | — | — | — | — | — |
| Butylated Hydroxytoluene | 0.025 | — | — | — | — | — | 0.025 | — | — | — |
| Polyethylene Glycol 3350 | — | — | — | — | 29.0 | — | — | — | — | — |
| Cholesterol | — | — | 0.5 | — | — | — | — | — | — | — |
| Acyclovir | — | — | — | — | — | 5.0 | — | — | — | — |
| Fragrance | 0.375 | — | 0.2 | — | 0.4 | — | 0.4 | — | — | — |
| Cerimide 1 | — | — | 0.002 | — | — | — | — | — | — | — |
| Purified Water | — | 98.83 | 91.78 | 76.2 | 81.2 | — | — | 98.95 | — | 98.95 |
| Clindamycin Phosphate | — | — | — | 1.0 | — | — | — | — | — | — |
| Polyethylene Glycol 600 | — | — | — | 5.0 | — | — | — | — | — | — |
| Miconazole Nitrate | 0.25 | — | — | — | — | — | — | — | — | — |
| Propylene Glycol | — | — | — | 15.7 | — | 25.0 | — | — | — | — |
| Trolamine | — | 0.23 | — | — | — | — | — | 0.23 | — | 0.23 |
| Sodium Hydroxyde 1.0M | — | — | — | q.s. | — | — | — | — | — | — |
| Isoproyl Myrisate | — | — | — | — | 4.3 | — | — | — | — | — |
| Cerimide 6-II | — | — | 0.5 | — | — | — | — | — | — | — |
| Phytosphingosine | — | — | 0.5 | — | — | — | — | — | — | — |

Example 3

Treatment of Dry and Scaly Skin

An exemplary hyaluronate composition according to the invention was used to treat dry and scaly skin. The exemplary hyaluronate composition used in this example contains about 0.1%, by mass, sodium hyaluronate having molecular weight substantially between about 1.6 million Daltons and about 2.8 million Daltons, and at least about 99%, by mass, water, and one or more preservatives and thickening agents (for example, about 0.2% methylparaben NF, about 0.02% propylparaben NF, about 0.3% carbomer 940 NF, about 0.15% trolamine NF).

An amount of the composition described above was provided in a suitable container-closure system to each of a group of patients. Each patient dispensed the composition from the container-closure system provided and applied the dispensed composition, two or three times daily, to areas of skin that were dry and scaly. Subsequent to the application that took place over the course of at least three weeks, it was observed that the areas of skin that had been dry and scaly were noticeably improved (i.e., less dry and scaly) or cured (i.e., not dry or scaly at all).

Example 4

Treatment of Ichthyosis

A pediatric patient was suffering from scaling and dryness of the skin. A medical conclusion was drawn that the patient had ichthyosis. An effective amount of the exemplary composition as described in Example 3 was administered topically to the patient b.i.d (twice a day), that is, by applying the composition to the areas of the patient's skin that were affected by scaling and dryness twice a day. Subsequent to the treatment that took place over the course of at least three weeks, the scaling and dryness had been greatly reduced.

Example 5

Treatment of Eczema

An approximately 14-year-old patient with eczema visited a university dermatology clinic. The patient's medical history indicated that the patient had suffered from eczema since the age of eight months. A physician at the clinic provided to the patient and the patient's mother, a registered nurse, an amount of the exemplary composition as described in Example 3 in a suitable container-closure system. The composition was applied topically at least once daily to the patient over the course of at least three weeks. It was subsequently observed that the eczema was significantly ameliorated.

Example 6

Treatment of Very Dry and Rough Skin

A pediatric patient had very dry and sensitive skin. A physician attending to the patient provided to the patient and the patient's mother an amount of the exemplary composition as described in Example 3 in a suitable container-closure system. The composition was applied topically at least once daily to the patient over the course of at least three weeks. It was subsequently observed that the very dry skin was significantly ameliorated and that the previously rough dry skin now appeared smooth.

Example 7

Treatment of Ezcema in a Seven-Month-Old Patient

An approximately seven-month-old patient with eczema visited a pediatrician. The patient had a family history of eczema; specifically, an older sibling and the child's father suffered from eczema. The patient was prescribed desoximatasone for topical administration to the most gravely affected areas. The results were not satisfactory. Subsequently, the pediatrician provided the patient's mother with an amount of the exemplary composition as described in Example 3 in a suitable container-closure system, for daily administration to the patient. After two or more weeks of topical administration of the composition (during which time the aforementioned topical dexosimatasone was not administered to the patient), patches of skin on the patient's head, the tops of the patient's shoulders, the outside edges of the patient's elbows, the patient's belly, the patient's thighs, and behind the patient's knees that had previously been observed as flaky and scaly now appeared far less flaky and scaly or normal. Redness that had previously been observed in those same areas was now observed to be completely abated.

Example 8

Treatment of Fungal Infection

A liberal amount of a composition according to Column A or G in Table 2 above is applied topically to an area of the skin of a human subject in need of treatment for a fungal infection. It is observed that, subsequent to a regimen of daily topical administration of the composition for several days, the subject's fungal infection is abated.

Example 9

Treatment of Bacterial Infection

A liberal amount of a composition according to Column D in Table 2 above is applied topically to the skin of a human subject in need of treatment for a bacterial infection. It is observed that, subsequent to a regimen of daily topical administration of the composition for several days, the subject's bacterial infection is abated.

Example 10

Treatment of Acne

A liberal amount of a composition according to Column E in Table 2 above is applied topically to the skin of a human subject in need of treatment for acne. It is observed that, subsequent to a regimen of daily topical administration of the composition for several days, the subject's acne is abated.

Example 11

Treatment of Viral Infection

A liberal amount of a composition according to Column F in Table 2 above is applied topically to the skin of a human subject in need of treatment for a viral infection of the integument. It is observed that, subsequent to a regimen of daily topical administration of the composition for several days, the subject's viral infection is abated.

Example 12

Treatment of Skin Disorders

A liberal amount of a composition according to any of the columns listed in Table 2 (for example, column B, C, H, I, or J) is applied topically to the skin of a human subject in need of treatment for eczema, dermatitis, atopic dermatitis, xerosis, psoriasis, inflammation, and/or diaper rash. It is observed that, subsequent to a regimen of daily topical administration of the composition for several days, the subject's eczema, dermatitis, atopic dermatitis, xerosis, psoriasis, inflammation, and/or diaper rash is abated.

EQUIVALENTS

The foregoing has been a description of certain non-limiting embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

INCORPORATION OF REFERENCES

All publications and patent documents cited in this application are incorporated by reference in their entirety to the same extent as if the contents of each individual publication or patent document were incorporated herein.

What is claimed is:

1. A composition suitable for topical administration to a mammalian subject, the composition comprising, by mass, from about 0.05% to about 5% of a sodium hyaluronate blend of at least three types of sodium hyaluronate with distinct molecular weight ranges and a pharmaceutically acceptable excipient,
   wherein from about 0.1 wt % to about 5 wt % of the sodium hyaluronate blend in the composition has a molecular weight ranging between about 0.01 megadaltons and about 0.4 megadaltons,
   wherein from about 0.1 wt % to about 5 wt % of the sodium hyaluronate blend in the composition has a molecular weight ranging between about 0.5 megadaltons and about 1.6 megadaltons, and
   wherein from about 50 wt % to about 95 wt % of the sodium hyaluronate blend in the composition has a molecular weight ranging between about 1.7 megadaltons and about 4.0 megadaltons;
   and wherein the pharmaceutically acceptable excipient is predominantly in the liquid phase at ambient temperature.

2. The composition according to claim 1, wherein the pharmaceutically acceptable excipient is selected from the group consisting of water, an alcohol, an oil, glycerin, polyethylene glycol, lanolin, petrolatum, wax, and poloxamer.

3. The composition according to claim 2, wherein the pharmaceutically acceptable excipient is alcohol selected from the group consisting of ethanol, benzyl alcohol, isopropyl alcohol, octyldodecanol, cetostearyl alcohol, and lanolin alcohol.

4. The composition according to claim 3, wherein the ratio of the mass of water to the total mass of the composition is about 99.235%.

5. The composition according to claim 2, wherein the pharmaceutically acceptable excipient is oil selected from the group consisting of almond oil, castor oil, corn oil, cottonseed oil, light mineral oil, mineral oil, olive oil, peanut oil, polyoxyl 35 castor oil, sesame oil, soybean oil, and sunflower oil.

6. The composition according to claim 2, wherein the pharmaceutically acceptable excipient is water.

7. The composition of claim 6, wherein the ratio of the mass of water to the total mass of the composition ranges from about 60% to about 99.9%.

8. The composition according to claim 6, wherein the ratio of the mass of water to the total mass of the composition ranges from about 90.0% to about 99.9%.

9. The composition according to claim 6, wherein the ratio of the mass of water to the total mass of the composition ranges from about 92.5% to about 99.8%.

10. The composition according to claim 6, wherein the ratio of the mass of water to the total mass of the composition ranges from about 95.0% to about 99.7%.

11. The composition according to claim 6, wherein the ratio of the mass of water to the total mass of the composition ranges from about 97.5% to about 99.6%.

12. The composition according to claim 6, wherein the ratio of the mass of water to the total mass of the composition ranges from about 98.5% to about 99.5%.

13. The composition according to claim 6, wherein the ratio of the mass of water to the total mass of the composition ranges from about 99.0% to about 99.4%.

14. The composition according to claim 6, wherein the ratio of the mass of water to the total mass of the composition ranges from about 99.2% to about 99.3%.

15. The composition of claim 1, wherein the composition further comprises an antifungal agent.

16. The composition according to claim 15, wherein the antifungal agent is selected from the group consisting of clioquinol, haloprogin, miconazole nitrate, povidone-iodine, tolnaftate, ketoconazole, undecylenic acid, butoconazole and clotrimazole.

17. The composition according to claim 16, wherein the antifungal agent is clotrimazole.

18. The composition according to claim 1, wherein the composition further comprises an antibiotic.

19. The composition according to claim 18, wherein the antibiotic is selected from the group consisting of bacitracin, bacitracin zinc, chlortetracycline hydrochloride, neomycin sulfate, clindamycin, erythromycin, and tetracycline hydrochloride.

20. The composition according to claim 1, wherein the composition further comprises an anti-acne agent.

21. The composition according to claim 20, wherein the anti-acne agent is selected from the group consisting of benzoyl peroxide, resorcinol, resorcinol monoacetate, salicylic acid, sulfur, adapalene, alitretinoin, etretinate, isotretinoin, tazarotene, and tretinoin.

22. The composition according to claim 21, wherein the anti-acne agent is benzoyl peroxide.

23. The composition according to claim 22, wherein the ratio of the mass of benzoyl peroxide to the total mass of the composition ranges from about 2.5% to about 10%.

24. The composition according to claim 1, wherein the composition further comprises an antiviral agent.

25. The composition according to claim 1, wherein the composition has an apparent viscosity of from about 10,000 centipoise to about 300,000 centipoise.

26. The composition according to claim 1, wherein the pH of the composition is from about 4 to about 8.

27. The composition according to claim 1, wherein the pharmaceutically acceptable excipient comprises white petrolatum.

28. The composition according to claim 27, wherein the composition further comprises butylated hydroxytoluene.

29. The composition according to claim 27, wherein the composition further comprises butylated hydroxyanisole.

30. The composition according to claim 1, wherein the composition further comprises butylated hydroxytoluene.

31. The composition according to claim 1, wherein the composition further comprises butylated hydroxyanisole.

32. The composition according to claim 1, wherein the composition further comprises one or more ceramides.

33. The composition according to claim 1, wherein the composition further comprises a corticosteroid.

34. The composition according to claim 33, wherein the corticosteroid is selected from the group consisting of betamethasone valerate, betamethasone dipropionate, dexamethasone acetate, dexamethasone sodium phosphate, hydrocortisone, hydrocortisone acetate, and hydrocortisone butyrate.

35. A composition suitable for maintaining or enhancing the moisture of skin, the composition comprising, by mass, at least about 80% water; a blend of at least three types of sodium hyaluronate with distinct molecular weight ranges,
    wherein from about 0.1 wt % to about 5 wt % of the sodium hyaluronate blend in the composition has a molecular weight ranging between about 0.01 megadaltons and about 0.4 megadaltons,
    wherein from about 0.1 wt % to about 5 wt % of the sodium hyaluronate blend in the composition has a molecular weight ranging between about 0.5 megadaltons and about 1.6 megadaltons, and
    wherein from about 50 wt % to about 95 wt % of the sodium hyaluronate blend in the composition has a molecular weight ranging between about 1.7 megadaltons and about 4.0 megadaltons;
    one or more preservatives; one or more thickening agents; and one or more bases;
    wherein the ratio of the mass of the sodium hyaluronate blend to the total mass of the composition is about 0.1%.

36. The composition of claim 35, wherein the one or more preservatives are selected from the group consisting of methylparaben, propylparaben, edetate sodium, benzalkonium chloride, and benzyl alcohol.

37. The composition of claim 36, wherein the one or more preservatives comprise methylparaben.

38. The composition of claim 36, wherein the one or more preservatives comprise propylparaben.

39. The composition of claim 36, wherein the one or more preservatives comprise methylparaben and propylparaben.

40. The composition of claim 36, wherein the one or more thickening agents are selected from the group consisting of carbomer 940, methyl cellulose, xanthan gum, carboxymethyl cellulose, hydroxypropyl cellulose, polyvinyl alcohol, one or more alginates, acacia, and one or more chitosans.

41. The composition of claim 40, wherein the one or more thickening agents comprise carbomer 940.

42. The composition of claim 35, wherein the one or more bases are selected from the group consisting of trolamine, sodium hydroxide, sodium bicarbonate, potassium hydroxide, magnesium hydroxide, calcium hydroxide, ammonium hydroxide, and potassium bicarbonate.

43. The composition of claim 42, wherein the one or more bases comprise trolamine.

44. The composition of claim 35, wherein the pH of the composition is between about 4 and about 8.

45. The composition of claim 35, wherein the composition has an absorbance of not more than 0.1 at 600 nm and a path of 1.0 cm and wherein the composition has a viscosity measured at temperature of 25 degree Celsius of not less than 5,000 centipoise and not more than 100,000 centipoise.

46. A composition suitable for maintaining or enhancing the moisture of skin, the composition comprising, by mass, at least about 95% water; 0.1% of a blend of at least three types of sodium hyaluronate with distinct molecular weight ranges,
   wherein from about 0.1 wt % to about 5 wt % of the sodium hyaluronate blend in the composition has a molecular weight ranging between about 0.01 megadaltons and about 0.4 megadaltons,
   wherein from about 0.1 wt % to about 5 wt % of the sodium hyaluronate blend in the composition has a molecular weight ranging between about 0.5 megadaltons and about 1.6 megadaltons,
   and wherein from about 50 wt % to about 95 wt % of the sodium hyaluronate blend in the composition has a molecular weight ranging between about 1.7 megadaltons and about 4.0 megadaltons;
   one or more preservatives; one or more thickening agents; and one or more bases;
   wherein the composition has an absorbance of not more than 0.1 at 600 nm and a path of 1.0 cm and wherein the composition has a viscosity measured at temperature of 25 degree Celsius of not less than 11,000 centipoise and not more than 18,000 centipoise.

47. A composition suitable for maintaining or enhancing the moisture of skin, the composition consisting essentially of, by mass, at least about 99% water; about 0.1% of a blend of at least three types of sodium hyaluronate with distinct molecular weight ranges,
   wherein from about 0.1 wt % to about 5 wt % of the sodium hyaluronate blend in the composition has a molecular weight ranging between about 0.01 megadaltons and about 0.4 megadaltons,
   wherein from about 0.1 wt % to about 5 wt % of the sodium hyaluronate blend in the composition has a molecular weight ranging between about 0.5 megadaltons and about 1.6 megadaltons,
   and wherein from about 50 wt % to about 95 wt % of the sodium hyaluronate blend in the composition has a molecular weight ranging between about 1.7 megadaltons and about 4.0 megadaltons;
   one or more preservatives; one or more thickening agents; and one or more bases.

48. A composition suitable for maintaining or enhancing the moisture of skin, the composition consisting essentially of, by mass:
   about 0.1% of a blend of at least three types of sodium hyaluronate with distinct molecular weight ranges,
   wherein from about 0.1 wt % to about 5 wt % of the sodium hyaluronate blend in the composition has a molecular weight ranging between about 0.01 megadaltons and about 0.4 megadaltons,
   wherein from about 0.1 wt % to about 5 wt % of the sodium hyaluronate in the composition has a molecular weight ranging between about 0.5 megadaltons and about 1.6 megadaltons,
   and wherein from about 50 wt % to about 95 wt % of the sodium hyaluronate blend in the composition has a molecular weight ranging between about 1.7 megadaltons and about 4.0 megadaltons;
   about 0.2% methylparaben;
   about 0.02% propylparaben;
   about 0.3% carbomer 940;
   about 0.15% trolamine; and
   about 99.23% water.

49. A method for treating a skin disorder on a mammalian subject, said method comprising administering to said subject an effective amount of the composition according to claim 1, wherein the skin disorder is selected from the group consisting of eczema, dermatitis, atopic dermatitis, xerosis, psoriasis, inflammation, diaper rash, fungal infection and acne.

50. The method according to claim 49, wherein the composition is administered at least once per day.

51. The method according to claim 50, wherein the composition is administered at least twice per day.

52. The method according to claim 51, wherein the composition is administered three times per day.

53. A process for manufacturing the composition according to claim 1, the process comprising the steps of:
   (a) admixing one or more preservatives, sodium hyaluronate, and one or more thickening agents to form a pre-water mixture;
   (b) admixing one or more bases and water to form a water mixture;
   (c) admixing the pre-water mixture and the water mixture to form a post-water mixture; and
   (d) homogenizing the post-water mixture to form the composition.

54. The process of claim 53, wherein step (a) comprises admixing methylparaben, propylparaben, sodium hyaluronate, and carbomer 940 in an approximate ratio, by mass, of 0.2:0.02:0.1:0.3 to form the pre-water mixture.

55. The process of claim 53, wherein step (b) comprises admixing trolamine and water in an approximate ratio, by mass, of 0.15:99.23 to form the water mixture.

56. The process of claim 53, wherein step (c) comprises admixing the pre-water mixture and the water mixture in an approximate ratio, by mass, of 0.62:99.38, to form a post-water mixture.

* * * * *